United States Patent
Lai et al.

(10) Patent No.: US 7,943,335 B2
(45) Date of Patent: May 17, 2011

(54) PROCESS FOR THE PRODUCTION OF DIACYLGLYCEROL

(75) Inventors: Oi Ming Lai, UPM Serdang (MY); Mohd Suria Affandi Yusoff, Banting (MY); Seong Koon Lo, UPM Serdang (MY); Kamariah Long, Serdang (MY); Chin Ping Tan, UPM Serdang (MY); Jew Yeok Lim, Banting (MY); Shawaluddin Tahiruddin, Banting (MY); Khairudin Hashim, Banting (MY)

(73) Assignees: Universiti Purra Malaysia (MY); Golden Hope Research Sendirian Berhard (MY)

( * ) Notice: Subject to any disclaimer, the term of this patent is extended or adjusted under 35 U.S.C. 154(b) by 467 days.

(21) Appl. No.: 12/159,430

(22) PCT Filed: Dec. 28, 2006

(86) PCT No.: PCT/MY2006/000034
§ 371 (c)(1),
(2), (4) Date: Jun. 27, 2008

(87) PCT Pub. No.: WO2007/075079
PCT Pub. Date: Jul. 5, 2007

(65) Prior Publication Data
US 2008/0312342 A1    Dec. 18, 2008

(30) Foreign Application Priority Data
Feb. 28, 2005 (MY) .............................. PI 20056218

(51) Int. Cl.
*C12Q 1/34* (2006.01)
(52) U.S. Cl. .......................................... 435/18; 435/159
(58) Field of Classification Search ................. 435/18, 435/159
See application file for complete search history.

(56) References Cited

U.S. PATENT DOCUMENTS

| | | |
|---|---|---|
| 4,678,580 A | 7/1987 | Brady et al. |
| 5,149,642 A | 9/1992 | Mazur et al. |
| 6,139,897 A | 10/2000 | Goto et al. |
| 6,261,812 B1 | 7/2001 | Yamada et al. |
| 6,361,980 B2 | 3/2002 | Sugiura et al. |
| 2003/0054082 A1 | 3/2003 | Koike et al. |

OTHER PUBLICATIONS

International Search Report for PCT/MY2006/000034, mailed on May 8, 2007.
Written Opinion of the International Searching Authority for PCT/MY2006/000034, mailed on May 8, 2007.

*Primary Examiner* — Tekchand Saidha
(74) *Attorney, Agent, or Firm* — The H.T. Than Law Group

(57) ABSTRACT

The present invention provides a process for producing a diacylglycerol, which comprises, reacting triacylglycerol with water and an enzyme preparation to obtain a mixture comprising of diacylglycerol, monoacylglycerol and free fatty acid; removing water content in the mixture by way of dehydration; and separating monoacylglycerol, free fatty acid and residual triacylglycerol by at least one separation method to obtain a high-purity diacylglycerol. An oil or fat composition comprising of diacylglycerol obtained from the process and phytosteryl esters and/or ferulic acid esters in an amount of from 0.5% to 25% by weight of diacylglycerol is also provided.

11 Claims, No Drawings

PROCESS FOR THE PRODUCTION OF DIACYLGLYCEROL

The present invention relates to the production of diacylglycerols. More particularly, the present invention relates to a process for producing a high-purity diacylglycerol at a high yield in a short period of time.

BACKGROUND TO THE INVENTION

Diacylglycerols are widely used in a variety of applications such as additives for improving plasticity of oils and fats, as well as edible oils in the food industry, and as a base material for the production of cosmetics and drugs. Generally, the preparation of such diacylglycerols involves an esterification reaction of glycerol with its corresponding fatty acid, an alcohol interchange reaction of glycerol with oil or fat, or the like, with the use of an alkali catalyst, or an enzyme such as a lipase, or the like. However, the use of an enzyme catalyst is preferable from the viewpoints of the yield and purity of the diacylglycerols synthesised and energy savings.

Japanese Patent Application No. 71495/1989 describes a lipase-catalysed reaction process that includes the reaction of a fatty acid or the like with glycerol in the presence of a 1,3-position selective lipase while removing water formed by the reaction outside the system to obtain a diacylglycerol at high yield and purity. The drawback of this process is that it is not able to investigate production conditions at an industrial level.

Japanese Patent Application No. 330289/1992 describes a process in which glycerol is added in an equimolar amount or more to a fatty acid to react. The reaction is stopped when the concentration of a diacylglycerol has been enhanced, insoluble glycerol is separated, and the reaction is further conducted while dehydrating, thereby synthesising diacylglycerol at a high esterification reaction rate by improving dehydration efficiency. This process involves technical difficulties such as necessity of stopping the reaction at the time the concentration of the diglyceride reaches a peak.

Japanese Patent Application No. 234391/1998 describes a process in which a mixture of a fatty acid or the like and glycerol or the like is reacted in a flow tube type reactor filled with a lipase while controlling the superficial velocity of the mixture in the reactor to at least 0.05 cm/s. This technique is easy to operate and can improve the reaction rate to some extent, but is insufficient in the purity of the resulting diglyceride and the industrial scale-up technique.

U.S. Pat. No. 6,361,980 describes a process for preparing diacylglycerol, which comprises of an enzyme-packed tower that includes an immobilised lipase preparation, carrying out an esterification reaction between: (1) an acyl group donor selected from the group consisting of a fatty acid, a lower alcohol ester thereof, and a mixture thereof; and (2) an acyl group acceptor selected from the group consisting of glycerol, a monoacylglycerol, and a mixture thereof; to obtain a reaction fluid from said enzyme-packed tower; reducing the water content or lower alcohol content in said reaction fluid; and subsequent to said reducing, recirculating the reaction fluid to said enzyme-packed tower, wherein a residence time of said reaction fluid in said enzyme-packed tower is 120 seconds or less; to obtain a diacylglycerol, wherein said reducing comprises dehydrating or de-alcoholising said reaction fluid is by feeding said reaction fluid though a spray nozzle, in a dehydration process. However, this process is costly as it requires the use of expensive purified fatty acids as raw material.

In view of the above, it would be advantageous to provide a process for producing a high-purity diacylglycerol at a high yield in a short period of time at an industrial level.

SUMMARY OF THE INVENTION

According to the present invention, there is provided a process for the production of a high-purity diacylglycerol at a high yield in a short period of time, said process comprising:
   reacting triacylglycerol with water and an enzyme preparation to obtain a mixture of diacylglycerol, monoacylglycerol and free fatty acid;
   removing water content in the mixture by way of dehydration; and
   separating the monoacylglycerol, free fatty acid and residual triacylglycerol by one or more separation methods to obtain a high-purity diacylglycerol.

According to the present invention, a high-purity diacylglycerol can be produced at a high-yield in a short period of time.

In another aspect of the present invention, there is provided an oil or fat composition comprising of diacylglycerol produced herein and phytosteryl esters and/or ferulic acid esters.

DESCRIPTION OF THE PREFERRED EMBODIMENTS

Various other objects, features and attendant advantages of the present invention will be more fully appreciated as the same becomes better understood from the following detailed description of the preferred embodiments of the invention.

The present invention provides a process for producing a high-purity diacylglycerol at a high yield and a short period of time. Where the features and details of the invention, either as steps of the invention or as combination of parts of the invention will now be described in greater detail. It will be understood to a person skilled in the art that the particular embodiments of the invention are shown by way of example illustration and not as limitations of the invention. While these examples are presented to show one skilled in the art how to operate within the scope of this invention, they are not to serve as a limitation on the scope of the invention where such scope is only defined in the claims.

The process for producing diacylglycerol in accordance with the present invention is comprised of the following steps:
   (i) reacting triacylglycerol with water and an enzyme preparation to obtain a mixture comprising of diacylglycerol, monoacylglycerol and free fatty acid;
   (ii) removing water content in the mixture by a dehydration method; and
   (iii) separating the monoacylglycerol, free fatty acid and residual triacylglycerol by one or more separation methods to obtain a high-purity diacylglycerol.

According to the present invention, step (i) involves controlled hydrolysis reaction which is conducted in the presence of water. From the viewpoint of enhancing the purity and production rate of the diacylglycerol, it is preferred that the amount of water in the reaction fluid is from 20 to 180 parts by weight per 100 parts by weight of the enzyme preparation.

It is preferred that the hydrolysis reaction in the present invention is controlled so that the amount of free fatty acids resulting from the controlled hydrolysis ranges from 5% to 50% by weight, preferably from 25% to 35% by weight.

The enzyme preparation used in the present invention is having a hydrolytic activity and comprises of a free enzyme or an immobilised enzyme.

It is preferred that the free enzyme or immobilised enzyme is a lipase.

The immobilised lipase enzyme is preferably immobilised onto a suitable enzyme carrier, such as an ion exchange resin. The lipase can possess non-position specific or 1,3-position specific.

Examples of free lipase enzymes or immobilised lipase enzymes that can be used in the present invention can be derived from microorganisms of the genera *Rhizopus, Aspergillus, Mucor, Candida* and/or *Pseudomonas*. For example, *Rhizopus delemar, Rhizopus japonicus, Rhizopus niveus, Aspergillus niger, Mucor javanicus, Mucor miehei, Candida rugosa, Candida antarctica, Pseudomonas cepacia* and the like. The immobilised lipase preparation is obtained by immobilising a lipase according to a known method for immobilising an enzyme.

Examples of preferred equipment for the controlled hydrolysis reaction used in the enzymatic method of the present invention include an agitation tank, a fixed bed, a fluidised tank, and combinations thereof. The controlled hydrolysis reaction can be conducted in a batchwise, continuous, or semi-continuous manner.

Since the controlled hydrolysis of the present invention is conducted by way of enzymatic hydrolysis, the controlled hydrolysis is carried out at a temperature within the operational temperature of the lipase, preferably from 20° C. to 90° C.

It is preferred that dehydration of the reaction fluid is conducted using conventional water removal methods such as centrifugation, condensation, distillation, evaporation or absorption.

The triacylglycerol used in the present invention includes conventional vegetable and animal fat or oil, or processed fats or oils comprising of $C_2$-$C_{24}$ saturated or unsaturated fatty acids or mixtures thereof, such as acetic acid, propionic acid, butyric acid, valeric acid, caproic acid, enanthic acid, caprylic acid, pelargonic acid, capric acid, undecanoic acid, lauric acid, myristic acid, myristoleic acid, palmitic acid, palmitoleic acid, zoomaric acid, stearic acid, oleic acid, elaidic acid, petroselinic acid, linoleic acid, α-linolenic acid, γ-linolenic acid, stearidonic acid, arachidic acid, arachidonic acid, gadoleic acid, arachic acid, dihomo-γ-linolenic acid, eicosapentaenoic acid, behenic acid, erucic acid, adrenic acid, docosapentaenoic acid, docosahexaenoic acid, nervonic acid, or an isomeric form thereof. Examples of vegetable and animal oil or fat which may be used in the present invention are canola oil, coconut oil, corn oil, cottonseed oil, palm oil, palm kernel oil, peanut oil, rapeseed oil, safflower oil, soybean oil, sunflower oil, olive oil, rice bran oil, corn bran oil, borage oil, evening primrose oil, flaxseed oil, grape seed oil, linseed oil, argania oil alfalfa oil, almond seed oil, apricot kernel oil, avocado oil, babassu oil, baobab oil, blackcurrant seed oil, brazil nut oil, cocoa seed oil, camellia oil, carrot oil, cashew nut oil, hazelnut oil, hemp seed oil, kiwi seed oil, *macadamia* nut oil, mango seed oil, melon seed oil, niger seed oil, peach kernel oil, *perilla* oil, pistachio oil, poppy seed oil, pumpkin seed oil, rambutan seed oil, rosehip oil, sesame oil, shea seed oil, tall oil, walnut oil and wheat germ oil, beef tallow, lard, fish oil; oil or fat obtained from the process of hardening, hydrogenation, transesterification, or randomisation, fractionation, distillation; and/or mixtures thereof.

The separation methods for use in separating monoacylglycerols, free fatty acids and residual triacylglycerols from diacylglycerols may be, for example deodorisation, steam distillation, molecular distillation, adsorption chromatography, and any combination of thereof. The separation methods may be conducted batchwise, continuous, and semi-continuous.

It is preferred that the process of the present invention is continuously performed until a final product containing diacylglycerol purity ranging from 10% to 96% is obtained.

Diacylglycerol purity, which in the present invention is defined as a ratio of diacylglycerol weight % to (diacylglycerol weight %+triacylglycerol weight %)×100 is used to measure the diacylglycerol concentration of the refined oil or fat composition used in the present invention. According to the present invention, a composition comprising of diacylglycerol ranging from 10% to 96% can be obtained. The resulting product may contain a small proportion of unhydrolysed triacylglycerol.

An oil or fat composition comprising of diacylglycerol produced from the process described herein and phytosteryl esters of fatty acids and/or ferulic acid esters can be obtained. The oil or fat composition obtained from the present invention can assist in lowering and preventing the risks of cardiovascular diseases and its underlying conditions such as hypercholesterolemia, hyperlipidemia, atherosclerosis, hypertension, thrombosis, as well as other diseases such as Type II diabetes, dementia, cancer, aging and those diseases which include oxidative damage as part of the disease pathology. Phytosteryl esters and/or ferulic acid esters are melted down, at temperatures ranging from 120° C. to 150° C., into a molten form before being mixed with the diacylglycerol oil produced from the present invention. The mixture is homogenised and allowed to cool at room temperature. The amount of phytosteryl esters and/or ferulic acid esters used in the present invention is preferably from 0.5% to 25% by weight of diacylglycerol.

Phytosterols, or plant sterols, are natural constituents of the human diet and are commonly found as minor constituents of vegetable oil. They are structurally related to cholesterol, but differ in their side-chain configuration. Phytosterols are generally extracted from by-products of either pulp and paper industry (wood-derived; "tall oil soap") or vegetable oil industry (vegetable-derived) using organic solvents (hexanes and acetone). A purified phytosterol mixture is white in colour (similar to cholesterol) with extremely low solubility. Similar to their appearance, cholesterol and phytosterols have similar chemical structures. There are a wide variety of phytosterols found in nature, but the most common ones are β-sitosterol, campesterol and stigmasterol. Phytosterols are naturally found in various parts of plants including oil-bearing seeds, nuts and fruits. Vegetable oil derived from these parts contain phytosterols in about 0.1 to 1.0 weight % of oil. In addition to their daily consumption, the use of phytosterols as cholesterol-lowering agents has been recently reconsidered. This resulted in marketing phytosterol-enriched food products ("functional foods") in North America and Europe. These products are intended to be used by a wide range of subjects including those with dyslipidemia. Although their pharmacological properties have not been fully explored, phytosterols have been effective in reducing plasma cholesterol levels without causing any serious side-effects. Phytosterols are also used in the treatment of cardiovascular diseases and its underlying conditions such as hypercholesterolemia, hyperlipidemia, atherosclerosis, hypertension, thrombosis, as well as other diseases such as Type II diabetes, dementia, cancer, aging and those diseases which include oxidative damage as part of the disease pathology.

Recently, studies have suggested that phytosteryl esters of fatty acids may result in a better outcome as compared to free phytosterols. Undissolved phytosterols have poor solubility in the micellar phase in the digestive tract and therefore are not capable of efficiently blocking cholesterol absorption. To increase the blood cholesterol lowering effect of phytosterols or its esters, it has to be homogenously dissolved in an oil or fat, such as edible oil or fat. However, phytosterols have a relatively lower solubility in oil or fat compared to their esters. Since phytosteryl esters have a relatively higher solubility in oil or fat than phytosterols, a higher concentration of these esters can be dissolved in oil or fat than phytosterols. Therefore, the physiological effects of phytosteryl esters can be made more effective and efficient than that of phytosterols.

Ferulic acid esters are known anti-oxidants which are generally more soluble in lipids. Ferulic acid esters comprise of oryzanols, more preferably γ-oryzanol, which can be found in rice and corn bran oils. Ferulic acids esters are known to be reducing the risks of cancer, lowering cholesterol level, and possess muscle-building property.

The oil or fat composition of the present invention can be used similarly to ordinary edible oils and fats, and can be applied to fat-processed foods, such as oil-in-water type fat-processed foods, drinks, desserts, ice-creams, dressings, toppings, mayonnaises, and sauces; water-in-oil type fat-processed foods such as margarines and spreads; processed fat foods such as peanut butters, frying and baking shortenings; processed foods such as potato chips, snack cakes, cakes, cookies, pies, pastries, breads, and chocolates; and other foods including bakery mixes, processed meat products, frozen entrees, and frozen foods.

It is also preferred that the oil or fat composition used in the present invention can be applied as a hypocholesteremic preparation in the form of a capsule, sugar-coated tablet, molded granules, candy, or drop.

The following examples illustrate the invention.

EXAMPLES

Example 1

In a 5 L flask, 1000 g of refined palm olein was mixed with 100 g of distilled water and 100 g of "Lipozyme RM IM", an immobilised 1,3-position selective lipase obtained from *Rhizomucor miehei* lipase. The mixture was reacted for 10 hours under stirring at 60° C. Thereafter, the lipase preparation was removed from the reaction product. Samples of the product were removed, and the amount of free fatty acids and partial acylglycerols was determined by gas chromatography. The results are shown in Table 1.

Example 2

In a 5 L flask, 1000 g of refined soybean oil was mixed with 100 g of distilled water and 100 g of "Lipozyme RM IM", an immobilised 1,3-position selective lipase obtained from *Rhizomucor miehei* lipase. The mixture was reacted for 10 hours under stirring at 60° C. Thereafter, the lipase preparation was removed from the reaction product. Samples of the product were removed, and the amount of free fatty acids and partial acylglycerols was determined by gas chromatography. The results are shown in Table 1.

TABLE 1

| Reaction components | Reactants before hydrolysis | | Hydrolysis product | |
|---|---|---|---|---|
| | Example 1 | Example 2 | Example 1 | Example 2 |
| Free Fatty acids (%) | 0.03 | 0.04 | 25.21 | 22.74 |
| Monoacylglycerols (%) | 0.93 | 1.17 | 21.98 | 23.22 |
| Diacylglycerols (%) | 2.64 | 3.36 | 41.56 | 43.68 |
| Triacylglycerols (%) | 96.40 | 95.43 | 11.25 | 10.36 |

Example 3

The hydrolysis products from Examples 1 and 2 were centrifuged at 5000 rpm for 10 minutes to separate the oil phase from the aqueous phase. The oil phase was subjected to molecular distillation at a temperature of 160° C. and at a pressure of 0.001 mbar to obtain the free fatty acids and monoacylglycerols as distillate 1 and diacylglycerol and triacylglycerol as residue 1. A further molecular distillation step at 210° C. and 0.001 mbar was performed to obtain the diacylglycerol as distillate 2 and triacylglycerol as residue 2. The results are shown in Table 2.

TABLE 2

| | Diacylglycerol purity (%) | |
|---|---|---|
| Hydrolysis product | Before purification | After purification |
| Example 1 | 41.56 | 88.70 |
| Example 2 | 43.68 | 90.83 |

Example 4

Prior to the addition of β-sitosteryl ester, approximately 200 grams of the purified diacylglycerol oil obtained from Example 1 was maintained at approximately 150° C. 16 grams of crystallised β-sitosteryl ester was added into the heated diacylglycerol oil and mixed for several minutes, while the temperature of the oil was allowed to cool slowly to room temperature.

Example 5

Prior to the addition of γ-oryzanol, approximately 200 g of the purified diacylglycerol oil obtained from Example 2 was maintained at approximately 150° C. 10 grams of crystallised γ-oryzanol was added into the heated diacylglycerol oil and mixed for several minutes, while the temperature of the oil was allowed to cool slowly to room temperature.

The invention claimed is:

1. A process for the production of diacylglycerol, said process comprising the steps of:
   (i) reacting triacylglycerol with water and a lipase enzyme preparation at a temperature ranging from 20° C. to 90° C. to obtain a mixture of diacylglycerol, monoacylglycerol and free fatty acid;
   (ii) removing water content in the mixture of step (i) by way of dehydration; and
   (iii) separating the monoacylglycerol, free fatty acid and residual triacylglycerol by at least one separation method to obtain a high-purity diacylglycerol;
   wherein the amount of water in the reaction mixture of step (i) is from 20 to 180 parts by weight per 100 parts by weight of the enzyme preparation and step (i) is conducted until between 5% and 50% of free fatty acids is obtained, thus producing diacylglycerol of up to 96% purity at a high yield in a short period of time.

2. A process according to claim 1, wherein the enzyme preparation in step (i) comprises of a free lipase or an immobilised lipase.

3. A process according to claim 2, wherein the immobilised lipase comprises of an immobilised non-position or 1,3-position selective lipase.

4. A process according to claim 2, wherein the free lipase or immobilised lipase is selected from the group consisting of lipases derived from microorganisms of the genera *Rhizopus, Aspergillus, Mucor, Candida* and *Pseudomonas*.

5. A process according to claim 1, wherein the triacylglycerol used in step (i) is selected from the group consisting of vegetable and animal fat or oil, and mixtures thereof.

6. A process according to claim 5, wherein the fat or oil is selected from the group consisting of canola oil, coconut oil, corn oil, cottonseed oil, palm oil, palm kernel oil, peanut oil, rapeseed oil, safflower oil, soybean oil, sunflower oil, olive oil, rice bran oil, corn bran oil, borage oil, evening primrose oil, flaxseed oil, grape seed oil, linseed oil, argania oil alfalfa oil, almond seed oil, apricot kernel oil, avocado oil, babassu oil, baobab oil, blackcurrant seed oil, brazil nut oil, cocoa seed oil, camellia oil, carrot oil, cashew nut oil, hazelnut oil, hemp seed oil, kiwi seed oil, macadamia nut oil, mango seed oil, melon seed oil, niger seed oil, peach kernel oil, perilla oil, pistachio oil, poppy seed oil, pumpkin seed oil, rambutan seed oil, rosehip oil, sesame oil, shea seed oil, tall oil, walnut oil and wheat germ oil, beef tallow, lard, fish oil; oils or fats obtained from the process of hardening, hydrogenation, trans-esterification, or randomisation, fractionation, distillation; and mixtures thereof.

7. A process according to claim 1, wherein the triacylglycerol comprises of saturated or unsaturated fatty acids comprising 2 to 24 carbon atoms.

8. A process according to claim 1, wherein the dehydration is carried out by way of centrifugation, condensation, distillation, evaporation or absorption.

9. A process according to claim 1, wherein the separation method is carried out by way of steam distillation, molecular distillation or adsorption chromatography.

10. A process according to claim 4, wherein the free lipase or immobilized lipase is selected from the group consisting of lipases derived from microorganisms of the species *Rhizopus delemar, Rhizopus japonicus, Rhizopus niveus, Aspergillus niger, Mucor javanicus, Mucor miehei, Candida rugosa, Candida Antarctica* and *Pseudomonas cepacia*.

11. A process according to claim 7, wherein the triacylglycerol is selected from the group consisting of acetic acid, propionic acid, butyric acid, valeric acid, caproic acid, enanthic acid, caprylic acid, pelargonic acid, capric acid, undecanoic acid, lauric acid, myristic acid, myristoleic acid, palmitic acid, palmitoleic acid, zoomaric acid, stearic acid, oleic acid, elaidic acid, petroselinic acid, linoleic acid, α-linolenic acid, γ-linolenic acid, stearidonic acid, arachidic acid, arachidonic acid, gadoleic acid, arachic acid, dihomo-γ-linolenic acid, eicosapentaenoic acid, behenic acid, erucic acid, adrenic acid, docosapentaenoic acid, docosahexaenoic acid, nervonic acid, an isomeric form thereof, fatty acids obtained by processing of oils or fats, hardening, hydrogenation, trans-esterification, or randomisation, fractionation, distillation; and mixtures thereof.

* * * * *